(12) United States Patent
Cordi et al.

(10) Patent No.: US 8,236,790 B2
(45) Date of Patent: Aug. 7, 2012

(54) BENZOTHIADIAZEPINE COMPOUNDS, A PROCESS FOR THEIR PREPARATION AND PHARMACEUTICAL COMPOSITIONS CONTAINING THEM

(75) Inventors: Alexis Cordi, Suresnes (FR); Patrice Desos, Bois-Colombes (FR); Pierre Lestage, Le Celle Saing Cloud (FR); Laurence Danober, Montesson (FR)

(73) Assignee: Les Laboratoires Servier, Suresnes Cedex (FR)

( * ) Notice: Subject to any disclaimer, the term of this patent is extended or adjusted under 35 U.S.C. 154(b) by 0 days.

(21) Appl. No.: 12/661,598

(22) Filed: Mar. 19, 2010

(65) Prior Publication Data
US 2010/0240635 A1 Sep. 23, 2010

(30) Foreign Application Priority Data
Mar. 20, 2009 (FR) .................................... 09 01300

(51) Int. Cl.
*C07D 285/36* (2006.01)
*A61K 31/554* (2006.01)
(52) U.S. Cl. .................................. 514/211.08; 540/545
(58) Field of Classification Search .................. 540/545; 514/211.08
See application file for complete search history.

(56) References Cited

U.S. PATENT DOCUMENTS
6,156,746 A 12/2000 Leftheris

FOREIGN PATENT DOCUMENTS
| EP | 1655030 | 5/2006 |
|----|---------|--------|
| WO | WO 9321170 | 10/1993 |
| WO | WO 9941246 | 8/1999 |
| WO | WO 03091232 | 11/2003 |

OTHER PUBLICATIONS

French Preliminary Search Report for FR0901300 of Jul. 21, 2009.
Advokat, et al., Neurosci. Biobehav. Rev., 1992, 16, 13-24.
Alt, et al., Biochemical Pharmacol., 2006, 71, 1273-1288.
Alt, et al., Curr. Pharm. Des., 2005, 11, 1511-1527.
Aracava, et al., J. Pharmacol. Exp. Ther., 2005, 312, 1195-1250.
Bai, et al., Neuropharmacol., 2003, 44, 1013-1021.
Beneyto, et al., Neuropsychopharmacol., 2007, 32, 1888-1902.
Bernard, et al., CNS Neurosci. Ther., 2010, 16, 193-212.
Black, Psychopharmacology, 2005, 179, 154-163.
Bliss, et al., Nature, 1993, 361, 31-39.
Chappell, et al., Neurology, 2007, 68, 1008-1012.
Damgaard, et al., Behav. Brain. Res., 2010, 207, 144-150.
Destot-Wong, et al., Neuropharmacol., 2009, 57, 277-286.
Diamond, et al., Neuron, 1995, 15, 1097-1107.
Dicou, et al., Brain Res., 2003, 970, 221-225.
Du, et al., Drug Discov. Today, 2006, 3, 519-526.
Ehlers, et al., Neuron, 2007, 54, 447-460.
Goff, et al., Neuropsychopharmacol., 2008, 33, 465-472.
Gogas, Curr. Opinion in Pharmacol., 2006, 6, 68-74.
Grigor'ev, et al., Bull. Experim. Biol. Med., 2003, 11, 535-538.
Hammond, et al., Neuropsychopharmacol., 2010, 35, 2110-2119.
Heine, et al., Science, 2008, 320, 201-205.
Hu, et al., Pharmacol. Biochem. Behay., 2011, in press.
Hu, et al., Proc. Nat. Acad. Sci., 2009, 106, 20504-20509.
Johnson, et al., J. Pharmacol. Exp. Ther., 1999, 289, 392-397.
Klyubin, et al., Neurobiol. Aging, 2011, 32, 614-623.
Knapp, et al., Eur. J. Pharmacol., 2002, 440, 27-35.
Legutko, et al., Neuropharmacology, 2001, 40, 1019-1027.
Lipina, et al., Neuropsychopharmacol., 2007, 32, 745-756.
Lockhart, et al., Eur. J. Pharmacol., 2007, 561, 23-31.
Losi, et al., Neuropharmacology, 2004, 46, 1105-1113.
Lu, et al., Brain Res., 1997, 768, 197-207.
Lynch, Curr. Opin. Pharmacol., 2006, 6, 82-88.
Lynch, et al., J. Pharmacol. Exp. Ther., 2002, 300, 717-723.
Lynch, et al., Trends Neurosci., 2006, 29, 554-562.
Maeng, et al., Biol. Psychiatry, 2008, 63, 349-352.
Malenka, et al., NY Acad. Sci., 2003, 1003, 1-11.
Malinow, Curr. Opin. Neurobiol. 2011, 22, 1-5.
Malinow, Science, 1994, 266, 1195-1196.
Manji, et al., Psychiatry, 2003, 53, 707-742.
Marenco, et al., CNS Drugs, 2006, 20, 173-185.
Maskell, et al., Br. J. Pharmacol., 2003, 140, 1313-1319.
Mathew, et al., Neuropsychopharmacol., 2008, 2, 1-13.
Michaelis, Prog. Neurobiol., 1998, 54, 369-415.
Olsen, et al., Pharmacol. Biochem. Behav., 2006, 84, 259-265.
O'Neill, et al., Curr. Drug Targets, 2007, 8, 603-620.
O'Neill, et al., Idrugs, 2007, 10, 185-192.
Ozawa, et al., Prog. Neurobiol., 1998, 54, 581-618.
Palmer, et al., Pharmacol. Rev., 2005, 57, 253-277.
Parsons, et al., Handb. Exp. Pharmacol., 2005, 169, 249-303.
Parsons, et al., Neuropharmacology, 1999, 38, 735-767.
Robbins, et al., Trends, Pharmacol. Sci., 2006, 27, 141-148.
Roger, et al., 9th Int. Conf. on Alzheimer's Disease & Related Disorders, Philadelphia 2004.

(Continued)

*Primary Examiner* — Bruck Kifle
(74) *Attorney, Agent, or Firm* — Hueschen and Sage

(57) ABSTRACT

Compounds of formula (I):

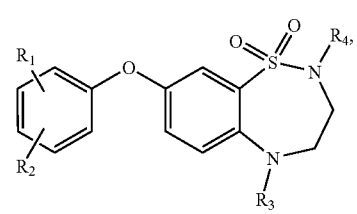

wherein:
$R_1$ and $R_2$, which may be the same or different, each represent a hydrogen or halogen atom or an alkyl, alkoxy, alkylthio, acyl, alkoxycarbonyl, carboxy, hydroxy, hydroxyalkyl, cyano, nitro, amino, substituted or unsubstituted aminocarbonyl, aminosulphonyl, alkylsulphonylaminoalkyl, N-hydroxy-carboximidamide or benzyloxy group,
$R_3$ represents a hydrogen atom or an alkyl, cycloalkyl or cycloalkylalkyl group,
$R_4$ represents a hydrogen atom or a substituted or unsubstituted alkyl group Medicinal products containing the same which are useful in treating or preventing conditions treatable by an AMPA receptor modulator and/or an NMDA receptor antagonist.

8 Claims, No Drawings

OTHER PUBLICATIONS

Rönicke, et al., Neurobiol. Aging, 2010, in press.
Sabbagh, et al., Curr. Opin. Investig. Drugs, 2010, 11, 80-91.
Sanacora, et al., Nat. Rev. Drug Discov., 2008, 7, 426-437.
Schinder, et al., Trends Neurosci., 2000, 23, 639-645.
Sellal, et al., Dement. Geriatr. Cogn. Disord., 2005, 19, 229-245.
Simmons, et al., Neurogbiol. Aging, 2011, 41, 436-444.
Simmons, et al., Proc. Nat. Acad. Sci., 2009, 105, 4906-4911.
Skolnick, et al., Trends Pharmacol. Sci., 2009, 30, 563-569.
Su, et al., Psychopharmacol., 2009, 206, 215-222.
Szewcyzyk, et al., Amino Acids, 2010, 39, 205-217.
Voss, et al., Neuropharmacol., 2007, 52, 590-597.
Whitlock, et al., Science, 2006, 313, 1093-1097.
Wollmuth, et al., Trends Neurosci., 2004, 27, 321-328.
Bartolini, et al., 1996, Pharmacol. Biochem, Behav., 1999, 53, 277-283.
Broberg, et al., Psychopharmacol., 2009, 206, 631-640.
Drian, et al., J. Neurosci. Res., 1999, 57, 927-934.
Ennaceur, et al., Behav. Brain Res., 1988, 31, 47-59.
Hunter, et al., Trends Pharmacol. Sci., 1995, 16, 123-128.
Macrae, et al., Br. J. Clin. Pharmacol., 1992, 34, 302-308.
Millan, et al., Nature Drug Discov., 2012, 11, 141-168.
Scali, et al., Neurosci. Lett., 1994, 170, 117-120.
Vandame et al., J, Neurochem., 2007, 103, 1682-1696.
Vandesquille, et al., Psychopharmacol., 2011, 215, 709-720.

BENZOTHIADIAZEPINE COMPOUNDS, A PROCESS FOR THEIR PREPARATION AND PHARMACEUTICAL COMPOSITIONS CONTAINING THEM

The present invention relates to new benzothiadiazepine compounds, to a process for their preparation, to pharmaceutical compositions containing them, and also to the use thereof as positive allosteric modulators of AMPA receptors and antagonists of NMDA receptors.

It has now been recognised that the excitatory amino acids, very especially glutamate, play a crucial role in the physiological processes of neuronal plasticity and in the mechanisms underlying learning and memory. Pathophysiological studies have clearly shown that a deficit in glutamatergic neurotransmission is closely linked to the development of Alzheimer's disease (Neuroscience and Biobehavioral Reviews, 1992, 16, 13-24; Progress in Neurobiology, 1992, 39, 517-545).

In addition, numerous works have demonstrated the existence of sub-types of excitatory amino acid receptors and their functional interactions (Molecular Neuropharmacology, 1992, 2, 15-31).

Among those receptors, the AMPA (α-amino-3-hydroxy-5-methyl-4-isoxazole-propionic acid) receptor is a receptor-channel for glutamate, which is permeable to $Na^+$ and $K^+$ and of low permeability to $Ca^{2+}$. The AMPA receptor appears to be involved to the greatest extent in fast physiological excitatory synaptic transmission and, especially, in memorisation processes. For example, it has been shown that learning is associated with an increase in the number of AMPA receptors in the synaptic contacts within the hippocampus, one of the areas of the brain essential to processes of memory and cognition. Likewise, nootropic agents such as aniracetam have been described as modulating the AMPA receptors of neuronal cells in a positive manner (J. Neurochemistry, 1992, 58, 1199-1204).

A second receptor, the NMDA (N-methyl-D-aspartate) receptor, also belongs to one of the three classes of glutamate receptor-channels. Binding of glutamate and its co-agonist, glycine, is necessary to result in opening of the channel and to allow entry of $Ca^{2+}$ into the cell (Progress in Neurobiology, 1998, 54, 581-618; Handb. Exp. Pharmacol., 2005, 169, 249-303). NMDA receptors likewise have an important physiological role in learning and memory. Nevertheless, excessive activation of these receptors, which may happen during cerebral ischaemia and cerebral anoxia, epileptic seizures, trauma or neurodegenerative diseases, results in excessive entry of $Ca^{2+}$ into the cell, which may have the potential to cause death of the cell due to a phenomenon of excitotoxicity (Progress in Neurobiology, 1998, 54, 369-415; J. Pharmacol. Exp. Ther., 2002, 300, 717-723). It has in fact been shown that certain forms of neurotoxicity caused by glutamate are dependent on an accumulation of $Ca^{2+}$ in the cell, which results in an increase in the metabolic stress on mitochondria and in increased production of free radicals. For these reasons, NMDA receptor antagonists have been developed for their neuroprotective properties, including memantine, which is currently indicated in the treatment of moderately severe to severe forms of Alzheimer's disease (Neuropharmacology, 1999, 38, 735-767; Dement. Geriatr. Cogn. Disord., 2005, 19, 229-245).

In the literature, very few compounds having a benzothiadiazine structure have been described as being positive modulators of AMPA receptors which also have NMDA receptor antagonist activity (Neuropharmacology, 2004, 46, 1105-1113). The compound IDRA-21, in particular, is capable of improving memory performance.

The patent specification WO 99/42456 describes, inter alia, benzothiadiazine and benzothiadiazepine compounds as modulators of AMPA receptors.

The benzothiadiazepine compounds to which the present invention relates, besides being new, exhibit pharmacological activities with respect to both the AMPA receptor and the NMDA receptor that are superior to those of compounds having similar structures described in the prior art.

More specifically, the present invention relates to compounds of formula (I):

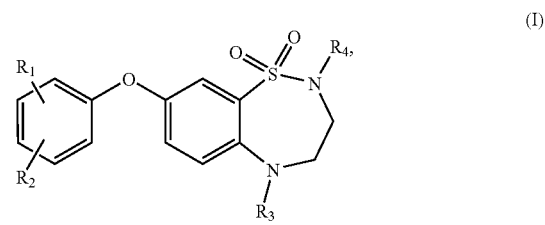

wherein:
$R_1$ and $R_2$, which may be the same or different, each represent a hydrogen atom; a halogen atom; or a linear or branched ($C_1$-$C_6$)alkyl group which is unsubstituted or substituted by one or more halogen atoms; a linear or branched ($C_1$-$C_6$)alkoxy group; a linear or branched ($C_1$-$C_6$)alkylthio group; a linear or branched ($C_1$-$C_6$)alkoxycarbonyl group; a carboxy group; a linear or branched ($C_1$-$C_6$)acyl group; a hydroxy group; a linear or branched ($C_1$-$C_6$)hydroxyalkyl group; a cyano group; a nitro group; an amino group which is unsubstituted or substituted by one or more linear or branched ($C_1$-$C_6$) alkyl groups; an amino group which is substituted by a linear or branched ($C_1$-$C_6$)acyl group; an aminocarbonyl group which is unsubstituted or substituted by one or more linear or branched ($C_1$-$C_6$)alkyl groups; an aminosulphonyl group which is unsubstituted or substituted by one or more linear or branched ($C_1$-$C_6$)alkyl groups; a ($C_1$-$C_6$)alkylsulphonylamino-($C_1$-$C_6$)alkyl group in which the alkyl moieties are linear or branched; an N-hydroxycarboximidamide group; or a benzyloxy group,
$R_3$ represents a hydrogen atom, a linear or branched ($C_1$-$C_6$)alkyl group, a ($C_3$-$C_8$)cycloalkyl group, or a ($C_3$-$C_8$)cycloalkyl-($C_1$-$C_6$)alkyl group in which the alkyl moiety is linear or branched,
$R_4$ represents a hydrogen atom or a linear or branched ($C_1$-$C_6$)alkyl group which is unsubstituted or substituted by one or more halogen atoms,
to their optical and positional isomers when they exist, and also to addition salts thereof with a pharmaceutically acceptable acid or base.

Among the pharmaceutically acceptable acids there may be mentioned, without implying any limitation, hydrochloric acid, hydrobromic acid, sulphuric acid, phosphoric acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, benzenesulphonic acid and camphoric acid.

Among the pharmaceutically acceptable bases there may be mentioned, without implying any limitation, sodium hydroxide, potassium hydroxide, triethylamine and tert-butylamine.

The group $R_1$ preferably represents a hydrogen atom or a hydroxy group; a linear or branched $(C_1-C_6)$hydroxyalkyl group and more especially a hydroxymethyl group; a linear or branched $(C_1-C_6)$alkoxycarbonyl group and advantageously an ethoxycarbonyl group; an amino group, or an aminocarbonyl group substituted by a linear or branched $(C_1-C_6)$alkyl group and more especially an N-methyl-aminocarbonyl group. Preference is given to the group $R_1$ being in the meta or para position. $R_1$ especially advantageously represents a hydrogen atom.

The groups $R_2$ and $R_4$ are each preferably a hydrogen atom.

$R_3$ preferably represents a hydrogen atom or a methyl group.

Preferred compounds of the invention are:
  8-phenoxy-2,3,4,5-tetrahydro-1,2,5-benzothiadiazepine 1,1-dioxide;
  ethyl 3-[(1,1-dioxido-2,3,4,5-tetrahydro-1,2,5-benzothiadiazepin-8-yl)oxy]-benzoate;
  3-[(1,1-dioxido-2,3,4,5-tetrahydro-1,2,5-benzothiadiazepin-8-yl)oxy]-N-methyl benzamide;
  {3-[(1,1-dioxido-2,3,4,5-tetrahydro-1,2,5-benzothiadiazepin-8-yl)oxy]phenyl}-methanol;
  4-[(1,1-dioxido-2,3,4,5-tetrahydro-1,2,5-benzothiadiazepin-8-yl)oxy]phenol;
  4-[(5-methyl-1,1-dioxido-2,3,4,5-tetrahydro-1,2,5-benzothiadiazepin-8-yl)oxy]phenol;
  4-[(1,1-dioxido-2,3,4,5-tetrahydro-1,2,5-benzothiadiazepin-8-yl)oxy]aniline.

Addition salts with a pharmaceutically acceptable acid or base of the preferred compounds of the invention form an integral part of the invention.

The invention relates also to a process for the preparation of compounds of formula (I), which process is characterised in that there is used as starting material a compound of formula (II):

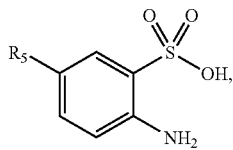

(II)

wherein $R_5$ represents a linear or branched $(C_1-C_6)$alkoxy group, which is reacted with thionyl chloride in the presence of dimethylformamide to yield the compound of formula (III):

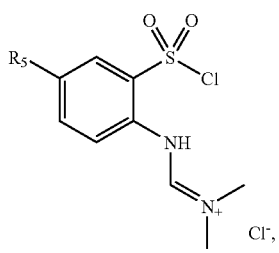

(III)

wherein $R_5$ is as defined hereinbefore, which is then subjected to the action of 2-chloroethylamine in a basic medium to yield the compound of formula (IV):

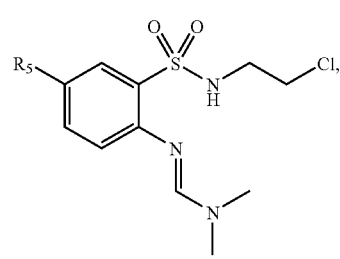

(IV)

wherein $R_5$ is as defined hereinbefore, which, after deprotection in an acid medium, is then cyclised to yield the compound of formula (V):

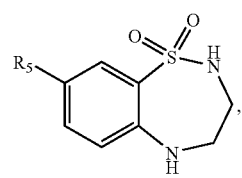

(V)

wherein $R_5$ is as defined hereinbefore, which is then subjected to the action of boron tribromide to yield the compound of formula (VI):

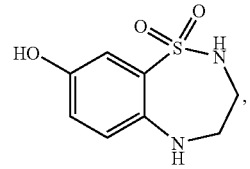

(VI)

which is reacted with a boronic acid compound of formula (VII):

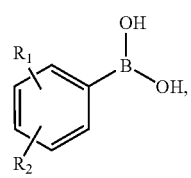

(VII)

wherein $R_1$ and $R_2$ are as defined for formula (I), to yield the compound of formula (I/a), a particular case of the compounds of formula (I):

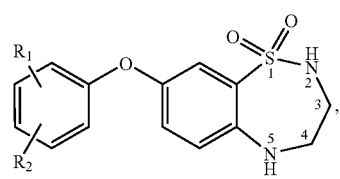

(I/a)

wherein $R_1$ and $R_2$ are as defined hereinbefore, a variant in the preparation of the compound of formula (I/a) consisting of using—once the step of coupling with the compound of formula (VI) has been carried out—conventional chemical reactions to subsequently modify the substituents of the boronic acid compound,
which compound of formula (I/a) may then, if required, be subjected to:
either double alkylation on the nitrogen atoms in positions 2 and 5, by action of a strong base in the presence of an alkylating agent R'-X wherein R' represents a linear or branched ($C_1$-$C_6$)alkyl group and X represents a halogen atom, to yield the compound of formula (I/b), a particular case of the compounds of formula (I):

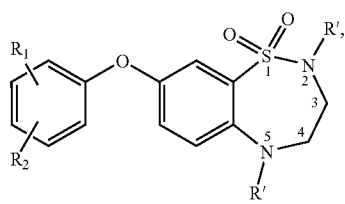

(I/b)

wherein $R_1$, $R_2$ and R' are as defined hereinbefore,
or alkylation on the nitrogen atom in position 2, by action of a base in the presence of an alkylating agent $R'_4$—X wherein $R'_4$ represents a linear or branched ($C_1$-$C_6$)alkyl group which is unsubstituted or substituted by one or more halogen atoms and X represents a halogen atom, to yield the compound of formula (I/c), a particular case of the compounds of formula (I):

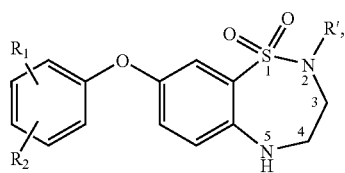

(I/c)

wherein $R_1$, $R_2$ and $R'_4$ are as defined hereinbefore,
which may optionally be subjected to alkylation on the nitrogen atom in position 5, by action of a base in the presence of an alkylating agent $R'_3$—X wherein $R'_3$ represents a linear or branched ($C_1$-$C_6$)alkyl group, a ($C_3$-$C_8$)cycloalkyl group or a ($C_3$-$C_8$)cycloalkyl-($C_1$-$C_6$)alkyl group in which the alkyl moiety is linear or branched, and X represents a halogen atom, to yield the compound of formula (I/d):

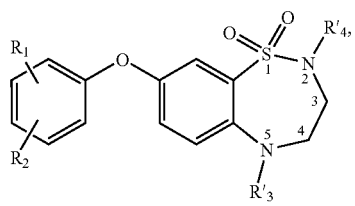

(I/b)

wherein $R_1$, $R_2$, $R'_3$ and $R'_4$ are as defined hereinbefore, or alternatively alkylation on the nitrogen atom in position 5, by means of a reductive amination reaction using a reducing agent such as sodium triacetoxyborohydride or cyanoborohydride in the presence of:
either [(1-ethoxycyclopropyl)oxy]trimethylsilane, or a compound of formula (VIII):

$R'''_3$—CHO  (VIII), wherein $R'''_3$ represents a hydrogen atom or a linear or branched ($C_1$-$C_5$)alkyl group, a ($C_3$-$C_8$)cycloalkyl group or a ($C_3$-$C_8$)cycloalkyl-($C_1$-$C_5$)group in which the alkyl moiety is linear or branched,
or alternatively a compound of formula (IX):

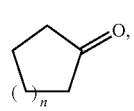

(IX)

wherein $0 \leq n \leq 4$,
to yield the compound of formula (I/e), a particular case of the compounds of formula (I):

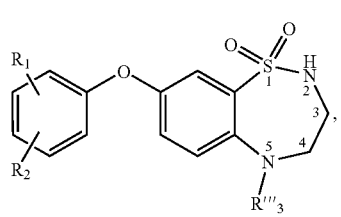

(I/e)

wherein $R'''_3$ represents a linear or branched ($C_1$-$C_6$) alkyl group, a ($C_3$-$C_8$)cyclo-alkyl group or a ($C_3$-$C_8$) cycloalkyl-($C_1$-$C_6$)group in which the alkyl moiety is linear or branched, and $R_1$ and $R_2$ are as defined hereinbefore,
which may optionally be subjected to alkylation on the nitrogen atom in position 2, by action of a base in the presence of an alkylating agent $R''_4$—X wherein $R''_4$ represents a linear or branched ($C_1$-$C_6$)alkyl group which is unsubstituted or substituted by one or more halogen atoms and X represents a halogen atom, to yield the compound of formula (I/f):

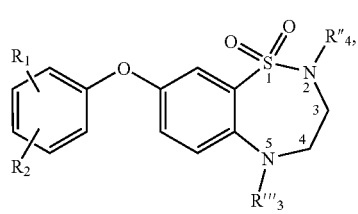

(I/f)

wherein $R_1$, $R_2$, $R'''_3$ and $R''_4$ are as defined hereinbefore,
which compounds of formulae (I/a) to (I/f), which constitute the totality of the compounds of formula (I), may then be purified according to a conventional separation technique, are converted, if desired, into their addition salts with a pharmaceutically acceptable acid or base and are separated, where appropriate, into their optical and positional isomers, if they exist, according to a conventional separation technique.
The compounds of formulae (II) and (VII) are commercially available or readily accessible to the person skilled in the art using conventional chemical reactions or chemical reactions described in the literature.

The compound of formula (VI) is new and, as an intermediate in the synthesis of compounds of formula (I), also forms part of the invention.

The compounds of formula (I) according to the invention have AMPA receptor activating properties and NMDA receptor antagonist properties, making them of use in the treatment or prevention of progressive neurodegenerative diseases, Alzheimer's disease, Parkinson's disease, Pick's disease, Huntington's chorea, Korsakoffs disease, schizophrenia, acute neurodegenerative diseases, frontal lobe and subcortical dementias, vascular dementias, epilepsy, cerebral vascular accidents and also depressive and anxious states.

The invention relates also to pharmaceutical compositions comprising, as active ingredient, at least one compound of formula (I) with one or more appropriate, inert, non-toxic excipients. Among the pharmaceutical compositions according to the invention there may be mentioned more especially those that are suitable for oral, parenteral (intravenous or subcutaneous), nasal, percutaneous, transcutaneous, rectal, perlingual, ocular and respiratory administration and especially tablets or dragées, sublingual tablets, sachets, paquets, capsules, lozenges, glossettes, suppositories, creams, ointments, dermal gels, injectable preparations and drinkable suspensions.

The useful dosage can be varied according to the nature and severity of the disorder, the administration route and also the age and weight of the patient, and it ranges from 0.01 mg to 1 g per day in one or more administrations.

The Examples that follow illustrate the invention but do not limit it in any way.

The starting materials used are products that are known or that are prepared according to known operating procedures.

The structures of the compounds described in the Examples were determined according to the usual spectrophotometric techniques (infrared, NMR, mass spectrometry).

EXAMPLE 1

8-phenoxy-2,3,4,5-tetrahydro-1,2,5-benzothiadiazepine 1,1-dioxide

Step A: N-[[[2-(chlorosulphonyl)-4-methoxyphenyl]amino]methylene]-N-methyl-methanaminium chloride Dimethylformamide (0.152 mol) is added dropwise to a suspension of 2-amino-5-methoxybenzenesulphonic acid (0.152 mol) in thionyl chloride (0.763 mol). The reaction mixture is heated very gradually to 70° C. and is maintained at that temperature for 1.5 hours. After cooling, the stirred reaction solution is treated by the addition of 20 ml of toluene. A precipitate is formed which is rapidly filtered off, rinsed with toluene and then dried at 40° C. in vacuo in the presence of KOH pellets, to yield the title product.

Step B: N-(2-chloroethyl)-2-{[(1E)-(dimethylamino)methylene]amino}-5-methoxybenzenesulphonamide Triethylamine (0.517 mol) is added dropwise to a suspension of a mixture of the product of the Step above (0.152 mol) and 2-chloroethylamine hydrochloride (0.182 mol) in 470 ml of dichloromethane, maintaining the temperature of the reaction mixture below 30° C. After stirring for 2 hours, the reaction mixture is diluted with dichloromethane and the organic phase is washed twice with water and then with saturated NaCl solution. The organic phase is dried over $MgSO_4$ and evaporated under reduced pressure. The residue is made more solid in ethyl ether to yield, after filtration, the title product.

Melting point: 89° C.

Elemental Microanalysis:

|  | C | H | N | S | Cl |
|---|---|---|---|---|---|
| theoretical % | 45.07 | 5.67 | 13.14 | 10.03 | 11.09 |
| experimental % | 44.93 | 5.63 | 13.07 | 10.19 | 11.82 |

Step C: 2-amino-N-(2-chloroethyl)-5-methoxybenzenesulphonamide

The entirety of the product from the Step above is suspended in a mixture of 130 ml of dioxane and 110 ml of 5M HCl. The reaction mixture is stirred at 110° C. for 16 hours. After evaporating off the dioxane, the reaction mixture is diluted with water and it is then neutralised by addition of 10% $NaHCO_3$ solution. At neutral pH, the aqueous phase is extracted 3 times with ethyl acetate. The organic phases are collected, washed with saturated NaCl solution and then dried over $MgSO_4$ to yield, after evaporation under reduced pressure, the title product in the form of an oil.

Step D: 8-methoxy-2,3,4,5-tetrahydro-1,2,5-benzothiadiazepine 1,1-dioxide

In a 1-litre PAAR autoclave reactor with a glass envelope, the entirety of the product from the Step above is suspended in 300 ml of ethanol. The reaction mixture is heated at 150° C. for 8 hours. After cooling is complete, the solid is filtered off to yield the title product.

Melting point: 126° C.

Step E: 2,3,4,5-tetrahydro-1,2,5-benzothiadiazepin-8-ol 1,1-dioxide

To a suspension of the product from the Step above (12.3 mmol) in 30 ml of dichloromethane there is added dropwise a 1M solution of boron tribromide in dichloromethane (37 ml), maintaining the temperature of the reaction mixture below 30° C. The heterogeneous mixture is stirred for 20 hours at ambient temperature and is poured onto about 100 g of ice. The solution is then neutralised by addition of 10% $Na_2CO_3$ solution. After evaporating the aqueous phase to dryness, the residue is triturated in acetone. The salts are filtered several times and the various filtrates (containing the expected product and also the starting material) are collected. These are absorbed onto silica to yield, after chromatographing by elution with a gradient of dichloromethane/acetone from 96/4 to 90/10 and making more solid in ethyl ether, the title product in the form of a white powder.

Melting point: 183-188° C.

Step F: 8-phenoxy-2,3,4,5-tetrahydro-1,2,5-benzothiadiazepine 1,1-dioxide

A suspension of phenylboronic acid (8.36 mmol), product from the Step above (5.60 mmol), $Cu(OAc)_2$ (8.42 mmol), pyridine (16.8 mmol) and 12 g of molecular sieve in 200 ml of dichloromethane is stirred overnight in air at ambient temperature. Acetone is then added and then the reaction mixture is filtered over a frit. The filtrate is evaporated, taken up in dichloromethane and chromatographed on a silica column, eluting with a mixture of dichloromethane/acetone 96/4, to yield, after making more solid in ethyl ether, the title product in the form of a white powder.

Melting point: 146-149° C.
Elemental Microanalysis:

|   | C | H | N | S |
|---|---|---|---|---|
| theoretical % | 57.92 | 4.56 | 9.65 | 11.04 |
| experimental % | 57.90 | 5.00 | 9.78 | 11.08 |

The products of Examples 2-9 that follow were obtained in accordance with the procedure of Step F of Example 1, starting from the intermediate 2,3,4,5-tetrahydro-1,2,5-benzothiadiazepin-8-ol 1,1-dioxide (Step E of Example 1) and the appropriate boronic acid as mentioned.

EXAMPLE 2

N-{4-[(1,1-dioxido-2,3,4,5-tetrahydro-1,2,5-benzothiadiazepin-8-yl)-oxy]benzyl}methanesulphonamide Reaction with (4-{[(methylsulphonyl)amino]methyl}phenyl)boronic acid.
Melting point: 115-117° C.
Elemental Microanalysis:

|   | C | H | N | S |
|---|---|---|---|---|
| theoretical % | 48.35 | 4.82 | 10.57 | 16.13 |
| experimental % | 48.60 | 4.93 | 10.50 | 16.20 |

EXAMPLE 3

8-(4-fluoro-phenoxy)-2,3,4,5-tetrahydro-1,2,5-benzothiadiazepine 1,1-dioxide

Reaction with (4-fluorophenyl)boronic acid.
Melting point: 153-156° C.
Elemental Microanalysis:

|   | C | H | N | S |
|---|---|---|---|---|
| theoretical % | 54.54 | 4.25 | 9.09 | 10.40 |
| experimental % | 54.14 | 4.41 | 9.04 | 10.08 |

EXAMPLE 4

8-(3-fluorophenoxy)-2,3,4,5-tetrahydro-1,2,5-benzothiadiazepine 1,1-dioxide

Reaction with (3-fluorophenyl)boronic acid.
Melting point: 128° C.
Elemental Microanalysis:

|   | C | H | N | S |
|---|---|---|---|---|
| theoretical % | 54.54 | 4.25 | 9.09 | 10.40 |
| experimental % | 54.39 | 4.17 | 8.99 | 9.98 |

EXAMPLE 5

8-(3,5-difluorophenoxy)-2,3,4,5-tetrahydro-1,2,5-benzothiadiazepine 1,1-dioxide

Reaction with (3,5-difluorophenyl)boronic acid.
Melting point: 90-95° C.
Elemental Microanalysis:

|   | C | H | N | S |
|---|---|---|---|---|
| theoretical % | 51.53 | 3.71 | 8.58 | 9.83 |
| experimental % | 51.44 | 3.86 | 8.50 | 9.65 |

EXAMPLE 6

3-[(1,1-dioxido-2,3,4,5-tetrahydro-1,2,5-benzothiadiazepin-8-yl)oxy]-benzonitrile Reaction with (3-cyanophenyl)boronic acid.
Melting point: 172-174° C.
Elemental Microanalysis:

|   | C | H | N | S |
|---|---|---|---|---|
| theoretical % | 57.13 | 4.15 | 13.33 | 10.17 |
| experimental % | 56.41 | 4.12 | 13.15 | 10.61 |

EXAMPLE 7 ethyl 3-[(1,1-dioxido-2,3,4,5-tetrahydro-1,2,5-benzothiadiazepin-8-yl)oxy]benzoate Reaction with [3-(ethoxycarbonyl)phenyl]boronic acid.
Melting point: 110° C.
Elemental Microanalysis:

|   | C | H | N | S |
|---|---|---|---|---|
| theoretical % | 56.34 | 5.01 | 7.73 | 8.85 |
| experimental % | 55.70 | 4.95 | 7.76 | 9.03 |

EXAMPLE 8

8-[4-(benzyloxy)phenoxy]-2,3,4,5-tetrahydro-1,2,5-benzothiadiazepine 1,1-dioxide Reaction with [4-(benzyloxy)phenyl]boronic acid.
Melting point: 134° C.

EXAMPLE 9

8-(4-nitrophenoxy)-2,3,4,5-tetrahydro-1,2,5-benzothiadiazepine 1,1-dioxide

Reaction with (4-nitrophenyl)boronic acid.
Melting point: 162° C.

EXAMPLE 10

3-[(1,1-dioxido-2,3,4,5-tetrahydro-1,2,5-benzothiadiazepin-8-yl)oxy]-N'-hydroxybenzenecarboximidamide To 750 µl of DMSO there are added hydroxylamine hydrochloride (1.90 mmol) and then triethylamine (1.90 mmol). An abundant white precipitate is formed, which is diluted by adding 3 ml of THF and stirring is carried out for 25 minutes at ambient temperature. The THF is evaporated off under reduced pressure and the suspension is filtered. The product of Example 6 (0.317 mmol) is added to the filtrate and the solution is stirred overnight at ambient temperature. After adding water to the reaction mixture, a gum forms which is made solid by adding dichloromethane and ethyl ether. The solid is filtered off and rinsed with water and ethyl ether to yield the title product.
Melting point: 197° C.
Elemental Microanalysis:

|                | C     | H    | N     | S    |
|----------------|-------|------|-------|------|
| theoretical %  | 51.71 | 4.63 | 16.08 | 9.20 |
| experimental % | 51.38 | 4.58 | 15.61 | 8.84 |

EXAMPLE 11

3-[(1,1-dioxido-2,3,4,5-tetrahydro-1,2,5-benzothiadiazepin-8-yl)oxy]benzoic acid A suspension of ester of Example 7 (0.55 mmol) in 5 ml of 1N sodium hydroxide solution is stirred for 30 minutes at 80° C. The reaction mixture is then neutralised using 1N HCl solution, extracted with ethyl acetate, washed (saturated NaCl solution), dried (MgSO$_4$), filtered and then evaporated under reduced pressure to yield, after triturating the residue in ethyl ether and filtering, the title product.
Melting point: 212-217° C.
Elemental Microanalysis:

|                | C     | H    | N    | S    |
|----------------|-------|------|------|------|
| theoretical %  | 53.89 | 4.22 | 8.38 | 9.59 |
| experimental % | 53.41 | 4.23 | 8.35 | 9.82 |

EXAMPLE 12

3-[(1,1-dioxido-2,3,4,5-tetrahydro-1,2,5-benzothiadiazepin-8-yl)oxy]-N-methylbenzamide The acid of Example 11 (0.66 mmol) is stirred overnight at ambient temperature in 50 ml of dichloromethane in the presence of 2-(1H-benzotriazol-1-yl)-1,1,3,3-tetramethyl-uronium tetrafluoroborate (0.80 mmol), diisopropylethylamine (0.80 mmol) and 2M methylamine solution in THF (1.32 mmol). The reaction mixture is then neutralised with 1N HCl solution, extracted with ethyl acetate, washed (saturated NaCl solution), dried (MgSO$_4$), filtered and then evaporated under reduced pressure to yield, after triturating the residue in a dichloromethane/methanol mixture and filtering, the title product.
Melting point: 205° C.
Elemental Microanalysis:

|                | C     | H    | N     | S    |
|----------------|-------|------|-------|------|
| theoretical %  | 55.32 | 4.93 | 12.10 | 9.23 |
| experimental % | 54.79 | 4.88 | 11.88 | 9.20 |

EXAMPLE 13

{3-[(1,1-dioxido-2,3,4,5-tetrahydro-1,2,5-benzothiadiazepin-8-yl)-oxy]phenyl}methanol The ester of Example 7 (0.805 mmol) is dissolved in 10 ml of THF, and LiAlH$_4$ (2.43 mmol) is added in small portions. After stirring for 30 minutes, 1 ml of isopropanol and 1 ml of brine are added to the reaction mixture in succession. The suspension is filtered, and the filtrate, after evaporation under reduced pressure, is chromatographed on a silica column (98/2 dichloromethane/methanol) to yield the title product.
Melting point: 146° C.

EXAMPLE 14

4-[(1,1-dioxido-2,3,4,5-tetrahydro-1,2,5-benzothiadiazepin-8-yl)oxy]-phenol

The product of Example 8 (0.76 mmol) is hydrogenated for 1 hour at atmospheric pressure in 60 ml of ethanol in the presence of 30 mg of 10% palladium-on-carbon and 2 drops of 4N HCl solution in dioxane. The catalyst is removed by filtration and the filtrate is evaporated to dryness. The residue is taken up in the hot state in ethyl acetate. The organic phase is washed with 1% NaHCO$_3$ solution and then with saturated NaCl solution, dried (MgSO$_4$), filtered and evaporated. The residue is triturated in a mixture of ethyl acetate/ethyl ether to yield, after filtration, the title product.
Melting point: 175° C.
Elemental Microanalysis:

|                | C     | H    | N    | S     |
|----------------|-------|------|------|-------|
| theoretical %  | 54.89 | 4.61 | 9.14 | 10.47 |
| experimental % | 54.96 | 4.74 | 8.89 | 10.39 |

EXAMPLE 15

8-[4-(benzyloxy)phenoxy]-5-methyl-2,3,4,5-tetrahydro-1,2,5-benzothiadiazepine 1,1-dioxide Aqueous formaldehyde 37% (12.6 mmol) is added to a suspension of the product of Example 8 (2.52 mmol) in 10 ml of acetonitrile. The suspension is stirred for 1 hour at ambient temperature. A spatula tip of bromocresol green and sodium cyanoborohydride (7.56 mmol) are added in succession. The reaction mixture is brought to acid pH by adding 4N HCl solution in dioxane. The reaction mixture is stirred overnight at ambient temperature and is then neutralised by addition of 10% NaHCO$_3$ solution. After diluting the reaction mixture with water, a precipitate forms, which is filtered off. Purification of the title product is carried out by chromatography on silica, eluting with a mixture of dichloromethane/ethyl acetate 96/4.

Melting point: 168-172° C.

EXAMPLE 16

4-[(5-methyl-1,1-dioxido-2,3,4,5-tetrahydro-1,2,5-benzothiadiazepin-8-yl)oxy]phenol The compound is obtained by catalytic hydrogenation of the product of Example 15 in accordance with the procedure of Example 14. Purification is carried out by chromatography on silica, eluting with a mixture of dichloromethane/acetone 95/5.

Melting point: 128-130° C.
Elemental Microanalysis:

|  | C | H | N | S |
|---|---|---|---|---|
| theoretical % | 56.24 | 5.03 | 8.74 | 10.01 |
| experimental % | 56.30 | 5.03 | 8.67 | 10.24 |

EXAMPLE 17

4-[(1,1-Dioxido-2,3,4,5-tetrahydro-1,2,5-benzothiadiazepin-8-yl)oxy]-aniline dihydrochloride The product of Example 9 (0.51 mmol) is hydrogenated for 2 hours at atmospheric pressure in 30 ml of methanol in the presence of 20 mg of 10% palladium-on-carbon. The catalyst is removed by filtration and the filtrate is evaporated to dryness. The residue is taken up in the hot state in methanol and the mixture is acidified with 4N HCl solution in dioxane. After evaporating to dryness, the residue is triturated in acetonitrile to yield, after filtration, the title product.

Melting point: 128-134° C.

The products of Examples 18-21 that follow are obtained by reductive alkylation of the compound of Example 1.

EXAMPLE 18

5-(Cyclopropylmethyl)-8-phenoxy-2,3,4,5-tetrahydro-1,2,5-benzothiadiazepine 1,1-dioxide hydrochloride To a solution of the product of Example 1 (1.38 mmol) in 50 ml of CH$_2$Cl$_2$ there are added cyclopropanecarbaldehyde (4.17 mmol), acetic acid (4.17 mmol) and sodium triacetoxyborohydride (4.17 mmol). The reaction mixture is stirred overnight at ambient temperature and is then neutralised by addition of 10% NaHCO$_3$ solution. After extracting with dichloromethane, the organic phases are collected, washed (saturated NaCl solution), dried (MgSO$_4$) and then evaporated. The crude product is purified by chromatography on silica (dichloromethane/methanol 98/2) and the product is converted into a salt in ethanol by adding 4N HCl solution in dioxane to yield the title product.

Melting point: 62° C. (meringue)

EXAMPLE 19

5-cyclobutyl-8-phenoxy-2,3,4,5-tetrahydro-1,2,5-benzothiadiazepine 1,1-dioxide The procedure is the same as that of Example 18 but the reaction mixture is stirred at 70° C. in the dichloroethane using cyclobutanone instead of the cyclopropanecarbaldehyde. The crude product is purified by chromatography on silica, eluting with a mixture of ethyl acetate/cyclohexane 2/8 to yield, after evaporation, the title product.

Melting point: 55° C. (meringue)
Elemental Microanalysis:

|  | C | H | N | S |
|---|---|---|---|---|
| theoretical % | 62.77 | 5.85 | 8.13 | 9.31 |
| experimental % | 62.81 | 5.90 | 7.98 | 9.34 |

EXAMPLE 20

5-methyl-8-phenoxy-2,3,4,5-tetrahydro-1,2,5-benzothiadiazepine 1,1-dioxide

The procedure is the same as that of Example 18, using aqueous formaldehyde 37% instead of the cyclopropanecarbaldehyde. The crude product is purified by chromatography on silica, eluting with a mixture of dichloromethane/methanol 98/2, to yield the title product.

Melting point: 128-131° C.
Elemental Microanalysis:

|  | C | H | N | S |
|---|---|---|---|---|
| theoretical % | 59.19 | 5.30 | 9.20 | 10.54 |
| experimental % | 59.35 | 5.30 | 9.07 | 10.52 |

EXAMPLE 21

5-ethyl-8-phenoxy-2,3,4,5-tetrahydro-1,2,5-benzothiadiazepine 1,1-dioxide

The procedure is the same as that of Example 18, using acetaldehyde instead of the cyclopropanecarbaldehyde. The crude product is purified by chromatography on silica, eluting with a mixture of dichloromethane/methanol 98/2, to yield the title product.

Melting point: 138° C.
Elemental Microanalysis:

|  | C | H | N | S |
|---|---|---|---|---|
| theoretical % | 60.36 | 5.70 | 8.80 | 10.07 |
| experimental % | 60.25 | 5.65 | 8.70 | 10.18 |

EXAMPLE 22

5-cyclopropyl-8-phenoxy-2,3,4,5-tetrahydro-1,2,5-benzothiadiazepine 1,1-dioxide The procedure is the same as that of Example 18 but the reaction mixture is stirred at 70° C. in the dichloroethane using [(1-ethoxycyclopropyl)oxy]trimethylsilane instead of the cyclopropanecarbaldehyde. The crude product is purified by chromatography on silica, eluting with a mixture of cyclohexane/ethyl acetate 70/30, to yield the title product.

Melting point: 119° C.

Elemental Microanalysis:

|  | C | H | N | S |
|---|---|---|---|---|
| theoretical % | 61.80 | 5.49 | 8.48 | 9.71 |
| experimental % | 61.15 | 5.53 | 8.25 | 9.60 |

EXAMPLE 23

2,5-dimethyl-8-phenoxy-2,3,4,5-tetrahydro-1,2,5-benzothiadiazepine 1,1-dioxide Sodium hydride 60% in mineral oil (3.05 mmol) is added to a suspension of the product of Example 1 (1.016 mmol) in 3 ml of dimethylformamide. After stirring for 10 minutes, a 2M solution of methyl iodide in methyl tert-butyl ether (3.05 mmol) is added dropwise.

The reaction mixture is stirred overnight at ambient temperature and is then diluted with water, extracted with ethyl acetate, washed (saturated NaCl solution), dried ($MgSO_4$), filtered and then evaporated to dryness. The residue is chromatographed on silica, eluting with a mixture of dichloromethane/acetone, to yield the title product.

Melting point: 130-131° C.

Elemental Microanalysis:

|  | C | H | N | S |
|---|---|---|---|---|
| theoretical % | 60.36 | 5.70 | 8.80 | 10.07 |
| experimental % | 60.58 | 5.75 | 8.64 | 10.31 |

EXAMPLE 24

2-(2-fluoroethyl)-8-phenoxy-2,3,4,5-tetrahydro-1,2,5-benzothiadiazepine 1,1-dioxide A suspension of the product of Example 1 (2.06 mmol) in 100 ml of acetonitrile is stirred for 24 hours in the presence of caesium carbonate (4.12 mmol) and 1-bromo-2-fluoroethane (4.12 mmol). The reaction mixture is then filtered and the filtrate is evaporated to dryness. The crude product is chromatographed on silica, eluting with a mixture of dichloromethane/methanol 98/2. The product is converted into a salt in ethanol by adding 4N HCl solution in dioxane to yield the title product in the form of a hydrochloride.

Melting point: 95-98° C.

Pharmacological Study

EXAMPLE A

Study of the Effect of Compounds on the Membrane Depolarisation Brought about by AMPA in Primary Cultures of Rat Neurons The test comprises the in vitro measurement, by means of fluorescence, of the membrane depolarisation brought about in cultured rat embryonic neurons by the joint action of AMPA and the compound under test, compared to the action of AMPA alone. The brain cells are placed in culture and kept in a cell culture incubator for 18 days. After incubation, the culture medium is withdrawn and replaced with fluorescent probe loading medium for measurement of the membrane potential (20 µl; membrane potential kit from Molecular Devices) and left at ambient temperature for 1 hour. The base fluorescence of the wells is read (FDSS apparatus from Hamamatsu) and the cells are then injected with AMPA (20 µl; concentration range: from 3 to 100 µM) and the action of the AMPA is measured kinetically. The test compound is then introduced into the wells (20 µl; in a concentration range crossed with that of AMPA) and the action of the compound is measured kinetically. At the end of each of the two periods of kinetic measurement, the result for each well is the average reading over the final 15 seconds of the period. The curves are plotted of the effect of AMPA at the various concentrations of compound. For each concentration of compound, the result is the area under the AMPA curve at that concentration, and the $EC_{2X}$ (the concentration of compound which doubles the membrane potential brought about by AMPA) is calculated.

The compounds of the invention greatly potentiate the excitatory effects of AMPA. By way of example, the compound of Example 1 has an $EC_{2X}$ of 25 µM.

EXAMPLE B

Object Recognition in the CD1 Mouse

The object recognition test (Behay. Brain Res., 1988, 31, 47-59) is based on the spontaneous exploratory activity of the animal and has the characteristics of episodic memory in humans. This memory test is sensitive to ageing (Eur. J. Pharmacol., 1997, 325, 173-180) and to cholinergic dysfunctions (Pharm. Biochem. Behay., 1996, 53(2), 277-283) and is based on the differences in the exploration of 2 objects of fairly similar shape—one familiar, the other new. The test procedure, which has been adapted for the CD1 mouse, comprises 3 phases which take place in the same test enclosure. During the first phase, which lasts 40 minutes, the mice are habituated to the environment. During the second phase, which takes place the next day, an object is placed in the enclosure and the mouse is free to explore it. Once the duration of that exploration has reached 20 seconds, the mouse is taken out of the enclosure. In the course of the third phase (5 minutes), 24 hours later, the same object is presented (acquiring the status of a "familiar" object), as well as a new object. The duration of exploration, expressed in seconds, is timed for each of the two objects. The control animals, which have previously been given the carrier by the oral route 60 minutes before each of the 3 phases, explore the "familiar" object and the "new" object for an equivalent period, which indicates that the object previously presented has been forgotten. Animals having received a compound that facilitates mnemocognition explore the new object preferentially, which indicates that the memory of the object previously presented has been retained.

When tested in accordance with the protocol of Example B, the compounds of formula (I) according to the invention have shown themselves to be effective in improving memorisation. For example, the results obtained with the compound of Example 1 of the present invention show significantly greater exploration of the new object, compared to the familiar object, at doses of 1 and 3 mg/kg PO.

EXAMPLE C

Effect of Compounds on the Current Induced by NMDA in Oocytes of *Xenopus laevis* Injected with Poly(A⁺) mRNA from Rat Cortex Electrophysiological recordings are carried out on oocytes of *Xenopus laevis* injected with poly($A^+$) mRNA from rat cortex and expressing, inter alia, NMDA-type glutamatergic receptors from rat cortex, in a plexiglass recording chamber continuously perfused with OR2 solution not containing magnesium (which blocks the opening of the NMDA receptor channel) and at ambient temperature. The inward current induced by an application of NMDA is recorded at a resting potential of −60 mV, using a standard two-electrode voltage clamp technique. The NMDA ($3 \times 10^{-4}$M) is applied with the perfusion solution in the presence of $3 \times 10^{-5}$M glycine for 30 seconds every 5 minutes, at a constant perfusion rate of 3 ml/min. The amplitude of the current induced by NMDA is measured at the peak of the current. The tested compounds are applied at increasing doses to the same oocyte in the perfusion solution 45 seconds before, 30 seconds during and 30 seconds after the application of $3 \times 10^{-4}$M NMDA in the presence of $3 \times 10^{-5}$M glycine every 5 minutes. The amplitude of the current induced by NMDA in the presence of compound is normalised and expressed as a percentage of that induced in the same oocyte in the absence of product, which corresponds to 100% response. The $IC_{50}$, which corresponds to the concentration of product which inhibits the current induced by NMDA by 50%, is determined by non-linear regression using a variable-slope sigmoid-shaped concentration-response model.

The compounds of the invention greatly inhibit the effects of NMDA. By way of example, the compound of Example 1 has an $IC_{50}$ of 9 µM.

EXAMPLE D

Pharmaceutical Composition

| Formula for the preparation of 1000 tablets each containing 10 mg of 8-phenoxy-2,3,4,5-tetrahydro-1,2,5-benzothiadiazepine 1,1-dioxide (Example 1) | 10 g |
|---|---|
| Hydroxypropylcellulose | 2 g |
| Wheat starch | 10 g |
| Lactose | 100 g |
| Magnesium stearate | 3 g |
| Talc | 3 g |

The invention claimed is:

1. A compound of formula (I):

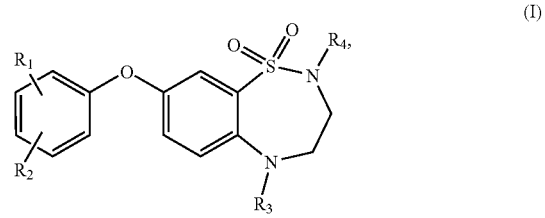

wherein:

$R_1$ and $R_2$, which may be the same or different, each represent a hydrogen atom; a halogen atom; a linear or branched ($C_1$-$C_6$)alkyl group which is unsubstituted or substituted by one or more halogen atoms; a linear or branched ($C_1$-$C_6$)alkoxy group; a linear or branched ($C_1$-$C_6$)alkylthio group; a linear or branched ($C_1$-$C_6$) alkoxycarbonyl group; a carboxy group; a linear or branched ($C_1$-$C_6$)acyl group; a hydroxy group; a linear or branched ($C_1$-$C_6$)hydroxyalkyl group; a cyano group; a nitro group; an amino group which is unsubstituted or substituted by one or more linear or branched ($C_1$-$C_6$) alkyl groups; an amino group which is substituted by a linear or branched ($C_1$-$C_6$)acyl group; an aminocarbonyl group which is unsubstituted or substituted by one or more linear or branched ($C_1$-$C_6$)alkyl groups; an aminosulphonyl group which is unsubstituted or substituted by one or more linear or branched ($C_1$-$C_6$)alkyl groups; a ($C_1$-$C_6$)alkyl-sulphonylamino-($C_1$-$C_6$)alkyl group in which the alkyl moieties are linear or branched; an N-hydroxycarboximidamide group; or a benzyloxy group, $R_3$ represents a hydrogen atom; a linear or branched ($C_1$-$C_6$)alkyl group; a ($C_3$-$C_8$)cycloalkyl group or a ($C_3$-$C_8$) cycloalkyl-($C_1$-$C_6$)alkyl group in which the alkyl moiety is linear or branched, $R_4$ represents a hydrogen atom or a linear or branched ($C_1$-$C_6$)alkyl group which is unsubstituted or substituted by one or more halogen atoms, or an optical isomer or addition salt thereof with a pharmaceutically acceptable acid or base.

2. The compound of claim 1, wherein $R_1$ represents a hydrogen atom, a hydroxy group, a hydroxymethyl group, an ethoxycarbonyl group, an amino group or an N-methylaminocarbonyl group.

3. The compound of claim 1, wherein $R_1$ is in the meta or para position.

4. The compound of claim 1, wherein $R_2$ and $R_4$ represent hydrogen atoms.

5. The compound of claim 1, wherein $R_3$ represents a hydrogen atom or a methyl group.

6. The compound of claim 1, which is selected from:
8-phenoxy-2,3,4,5-tetrahydro-1,2,5-benzothiadiazepine 1,1-dioxide;
ethyl 3-[(1,1-dioxido-2,3,4,5-tetrahydro-1,2,5-benzothiadiazepin-8-yl)oxy]-benzoate;
3-[(1,1-dioxido-2,3,4,5-tetrahydro-1,2,5-benzothiadiazepin-8-yl)oxy]-N-methyl-benzamide;
{3-[(1,1-dioxido-2,3,4,5-tetrahydro-1,2,5-benzothiadiazepin-8-yl)oxy]phenyl}-methanol;
4-[(1,1-dioxido-2,3,4,5-tetrahydro-1,2,5-benzothiadiazepin-8-yl)oxy]phenol;
4-[(5-methyl-1,1-dioxido-2,3,4,5-tetrahydro-1,2,5-benzothiadiazepin-8-yl)oxy]-phenol;
4-[(1,1-dioxido-2,3,4,5-tetrahydro-1,2,5-benzothiadiazepin-8-yl)oxy]aniline,
and addition salts thereof with a pharmaceutically acceptable acid or base.

7. A compound of formula (VI):

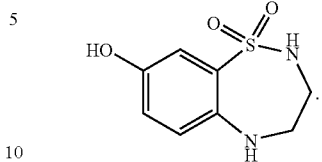

(VI)

8. A pharmaceutical composition comprising as active ingredient a compound of claim 1, in combination with one or more pharmaceutically acceptable, non-toxic, inert carriers.

* * * * *

UNITED STATES PATENT AND TRADEMARK OFFICE
CERTIFICATE OF CORRECTION

PATENT NO. : 8,236,790 B2
APPLICATION NO. : 12/661598
DATED : August 7, 2012
INVENTOR(S) : Alexis Cordi et al.

It is certified that error appears in the above-identified patent and that said Letters Patent is hereby corrected as shown below:

Title Page, item (73) Assignee: "Les Laboratories Servier" should be --Les Laboratoires Servier--.

Title Page 2, item (56), Other Publications, Col. 2, line 3; BARTOLINI: "1999" should be --1996--.

Signed and Sealed this
Twenty-third Day of October, 2012

David J. Kappos
*Director of the United States Patent and Trademark Office*